(12) United States Patent
Boesen

(10) Patent No.: US 10,015,579 B2
(45) Date of Patent: Jul. 3, 2018

(54) AUDIO ACCELEROMETRIC FEEDBACK THROUGH BILATERAL EAR WORN DEVICE SYSTEM AND METHOD

(71) Applicant: BRAGI GmbH, München (DE)

(72) Inventor: Peter Vincent Boesen, München (DE)

(*) Notice: Subject to any disclaimer, the term of this patent is extended or adjusted under 35 U.S.C. 154(b) by 0 days.

(21) Appl. No.: 15/481,623

(22) Filed: Apr. 7, 2017

(65) Prior Publication Data

US 2017/0295443 A1    Oct. 12, 2017

Related U.S. Application Data

(60) Provisional application No. 62/320,147, filed on Apr. 8, 2016.

(51) Int. Cl.
*H04R 25/00* (2006.01)
*H04R 1/10* (2006.01)
*A61B 5/11* (2006.01)
*A61B 5/00* (2006.01)
*G06F 3/01* (2006.01)
*H04S 7/00* (2006.01)

(52) U.S. Cl.
CPC .......... *H04R 1/1041* (2013.01); *A61B 5/1114* (2013.01); *A61B 5/486* (2013.01); *G06F 3/012* (2013.01); *H04R 1/1016* (2013.01); *A61B 5/6817* (2013.01); *A61B 2503/10* (2013.01); *A61B 2562/0219* (2013.01); *H04R 2460/07* (2013.01); *H04R 2460/13* (2013.01); *H04S 7/304* (2013.01)

(58) Field of Classification Search
USPC .... 381/23.1, 58, 59, 62, 309, 386, 387, 312, 381/326, 380
See application file for complete search history.

(56) References Cited

U.S. PATENT DOCUMENTS 3,934,100 A    1/1976 Harada
4,150,262 A    4/1979 Ono
(Continued)

FOREIGN PATENT DOCUMENTS

CN    204244472 U    4/2015
CN    104683519 A    6/2015
(Continued)

OTHER PUBLICATIONS

Akkermans, "Acoustic Ear Recognition for Person Identification", Automatic Identification Advanced Technologies, 2005 pp. 219-223.
(Continued)

*Primary Examiner* — Yosef K Laekemariam
(74) *Attorney, Agent, or Firm* — Goodhue, Coleman & Owens, P.C.

(57) ABSTRACT

A system includes at least one earpiece having at least one sensor, at least one speaker, and at least one processor capable of ascertaining a desired position for a user's head in order to guide the user as to the desired position for the user's head. A method it determining a current orientation of a user's head, calculating a desired position for the user's head in relation to the current orientation of the user's head, creating an audio signal containing instructions to guide the user as to the desired position for the user's head, and transmitting the audio signal to a user's ears.

16 Claims, 4 Drawing Sheets

(56) References Cited

U.S. PATENT DOCUMENTS

| | | |
|---|---|---|
| 4,334,315 A | 6/1982 | Ono et al. |
| 4,375,016 A | 2/1983 | Harada |
| 4,588,867 A | 5/1986 | Konomi |
| 4,654,883 A | 3/1987 | Iwata |
| 4,682,180 A | 7/1987 | Gans |
| 4,791,673 A | 12/1988 | Schreiber |
| 4,865,044 A | 9/1989 | Wallace et al. |
| 5,191,602 A | 3/1993 | Regen et al. |
| 5,201,007 A | 4/1993 | Ward et al. |
| 5,280,524 A | 1/1994 | Norris |
| 5,295,193 A | 3/1994 | Ono |
| 5,298,692 A | 3/1994 | Ikeda et al. |
| 5,343,532 A | 8/1994 | Shugart |
| 5,363,444 A | 11/1994 | Norris |
| 5,497,339 A | 3/1996 | Bernard |
| 5,606,621 A | 2/1997 | Reiter et al. |
| 5,613,222 A | 3/1997 | Guenther |
| 5,692,059 A | 11/1997 | Kruger |
| 5,721,783 A | 2/1998 | Anderson |
| 5,749,072 A | 5/1998 | Mazurkiewicz et al. |
| 5,771,438 A | 6/1998 | Palermo et al. |
| 5,802,167 A | 9/1998 | Hong |
| 5,929,774 A | 7/1999 | Charlton |
| 5,933,506 A | 8/1999 | Aoki et al. |
| 5,949,896 A | 9/1999 | Nageno et al. |
| 5,987,146 A | 11/1999 | Pluvinage et al. |
| 6,021,207 A | 2/2000 | Puthuff et al. |
| 6,054,989 A | 4/2000 | Robertson et al. |
| 6,081,724 A | 6/2000 | Wilson |
| 6,094,492 A | 7/2000 | Boesen |
| 6,111,569 A | 8/2000 | Brusky et al. |
| 6,112,103 A | 8/2000 | Puthuff |
| 6,157,727 A | 12/2000 | Rueda |
| 6,167,039 A | 12/2000 | Karlsson et al. |
| 6,181,801 B1 | 1/2001 | Puthuff et al. |
| 6,208,372 B1 | 3/2001 | Barraclough |
| 6,230,029 B1 | 5/2001 | Yegiazaryan et al. |
| 6,275,789 B1 | 8/2001 | Moser et al. |
| 6,339,754 B1 | 1/2002 | Flanagan et al. |
| 6,408,081 B1 | 6/2002 | Boesen |
| 6,424,820 B1 | 7/2002 | Burdick et al. |
| D464,039 S | 10/2002 | Boesen |
| 6,470,893 B1 | 10/2002 | Boesen |
| D468,299 S | 1/2003 | Boesen |
| D468,300 S | 1/2003 | Boesen |
| 6,542,721 B2 | 4/2003 | Boesen |
| 6,560,468 B1 | 5/2003 | Boesen |
| 6,654,721 B2 | 11/2003 | Handelman |
| 6,664,713 B2 | 12/2003 | Boesen |
| 6,694,180 B1 | 2/2004 | Boesen |
| 6,718,043 B1 | 4/2004 | Boesen |
| 6,738,485 B1 | 5/2004 | Boesen |
| 6,748,095 B1 | 6/2004 | Goss |
| 6,754,358 B1 | 6/2004 | Boesen et al. |
| 6,784,873 B1 | 8/2004 | Boesen et al. |
| 6,823,195 B1 | 11/2004 | Boesen |
| 6,852,084 B1 | 2/2005 | Boesen |
| 6,879,698 B2 | 4/2005 | Boesen |
| 6,892,082 B2 | 5/2005 | Boesen |
| 6,920,229 B2 | 7/2005 | Boesen |
| 6,952,483 B2 | 10/2005 | Boesen et al. |
| 6,987,986 B2 | 1/2006 | Boesen |
| 7,136,282 B1 | 11/2006 | Rebeske |
| 7,203,331 B2 | 4/2007 | Boesen |
| 7,209,569 B2 * | 4/2007 | Boesen ............ H04M 1/6066 340/575 |
| 7,215,790 B2 | 5/2007 | Boesen et al. |
| 7,463,902 B2 | 12/2008 | Boesen |
| 7,508,411 B2 | 3/2009 | Boesen |
| 7,825,626 B2 | 11/2010 | Kozisek |
| 7,979,035 B2 | 7/2011 | Griffin et al. |
| 7,983,628 B2 | 7/2011 | Boesen |
| 8,095,188 B2 | 1/2012 | Shi |
| 8,140,357 B1 | 3/2012 | Boesen |
| 8,300,864 B2 | 10/2012 | Müllenborn et al. |
| 8,436,780 B2 | 5/2013 | Schantz et al. |
| 8,719,877 B2 | 5/2014 | VonDoenhoff et al. |
| 8,891,800 B1 | 11/2014 | Shaffer |
| 8,994,498 B2 | 3/2015 | Agrafioti et al. |
| 9,013,145 B2 | 4/2015 | Castillo et al. |
| 9,037,125 B1 | 5/2015 | Kadous |
| 9,081,944 B2 | 7/2015 | Camacho et al. |
| 9,510,159 B1 | 11/2016 | Cuddihy et al. |
| 2001/0005197 A1 | 6/2001 | Mishra et al. |
| 2001/0027121 A1 | 10/2001 | Boesen |
| 2001/0056350 A1 | 12/2001 | Calderone et al. |
| 2002/0002413 A1 | 1/2002 | Tokue |
| 2002/0007510 A1 | 1/2002 | Mann |
| 2002/0010590 A1 | 1/2002 | Lee |
| 2002/0030637 A1 | 3/2002 | Mann |
| 2002/0046035 A1 | 4/2002 | Kitahara et al. |
| 2002/0057810 A1 | 5/2002 | Boesen |
| 2002/0076073 A1 | 6/2002 | Taenzer et al. |
| 2002/0118852 A1 | 8/2002 | Boesen |
| 2003/0002705 A1 | 1/2003 | Boesen |
| 2003/0065504 A1 | 4/2003 | Kraemer et al. |
| 2003/0100331 A1 | 5/2003 | Dress et al. |
| 2003/0104806 A1 | 6/2003 | Ruef et al. |
| 2003/0115068 A1 | 6/2003 | Boesen |
| 2003/0125096 A1 | 7/2003 | Boesen |
| 2003/0218064 A1 | 11/2003 | Conner et al. |
| 2004/0070564 A1 | 4/2004 | Dawson et al. |
| 2004/0160511 A1 | 8/2004 | Boesen |
| 2005/0017842 A1 | 1/2005 | Dematteo |
| 2005/0043056 A1 | 2/2005 | Boesen |
| 2005/0125320 A1 | 6/2005 | Boesen |
| 2005/0148883 A1 | 7/2005 | Boesen |
| 2005/0165663 A1 | 7/2005 | Razumov |
| 2005/0196009 A1 | 9/2005 | Boesen |
| 2005/0251455 A1 | 11/2005 | Boesen |
| 2005/0266876 A1 | 12/2005 | Boesen |
| 2006/0029246 A1 | 2/2006 | Boesen |
| 2006/0074671 A1 | 4/2006 | Farmaner et al. |
| 2006/0074808 A1 | 4/2006 | Boesen |
| 2006/0166715 A1 | 7/2006 | Engelen et al. |
| 2006/0258412 A1 | 11/2006 | Liu |
| 2008/0090622 A1 | 4/2008 | Kim et al. |
| 2008/0146890 A1 | 6/2008 | LeBoeuf et al. |
| 2008/0254780 A1 | 10/2008 | Kuhl et al. |
| 2009/0017881 A1 | 1/2009 | Madrigal |
| 2009/0073070 A1 | 3/2009 | Rofougaran |
| 2009/0296968 A1 | 12/2009 | Wu et al. |
| 2010/0033313 A1 | 2/2010 | Keady et al. |
| 2010/0203831 A1 | 8/2010 | Muth |
| 2010/0320961 A1 | 12/2010 | Castillo et al. |
| 2011/0286615 A1 | 11/2011 | Olodort et al. |
| 2014/0122116 A1 | 5/2014 | Smythe |
| 2014/0163771 A1 | 6/2014 | Demeniuk |
| 2014/0185828 A1 | 7/2014 | Helbling |
| 2014/0222462 A1 | 8/2014 | Shakil et al. |
| 2014/0270227 A1 | 9/2014 | Swanson |
| 2014/0270271 A1 | 9/2014 | Dehe et al. |
| 2015/0028996 A1 | 1/2015 | Agrafioti et al. |
| 2015/0148989 A1 | 5/2015 | Cooper et al. |
| 2015/0245127 A1 | 8/2015 | Shaffer |
| 2016/0033280 A1 | 2/2016 | Moore et al. |
| 2016/0073189 A1 | 3/2016 | Linden et al. |

FOREIGN PATENT DOCUMENTS

| | | |
|---|---|---|
| CN | 104837094 A | 8/2015 |
| EP | 1017252 A2 | 7/2000 |
| EP | 2903186 A1 | 8/2015 |
| GB | 2074817 | 4/1981 |
| GB | 2508226 A | 5/2014 |
| JP | 06292195 | 10/1998 |
| WO | 2008103925 A1 | 8/2008 |
| WO | 2007034371 A3 | 11/2008 |
| WO | 2011001433 A2 | 1/2011 |
| WO | 2012071127 A1 | 5/2012 |
| WO | 2013134956 A1 | 9/2013 |
| WO | 2014043179 A2 | 3/2014 |
| WO | 2015061633 A2 | 4/2015 |

(56) References Cited

FOREIGN PATENT DOCUMENTS

| WO | 2015110577 A1 | 7/2015 |
|---|---|---|
| WO | 2015110587 A1 | 7/2015 |
| WO | 2016032990 A1 | 3/2016 |

OTHER PUBLICATIONS

Announcing the $3,333,333 Stretch Goal (Feb. 24, 2014).
Ben Coxworth: "Graphene-based ink could enable low-cost, foldable electronics", "Journal of Physical Chemistry Letters", Northwestern University, (May 22, 2013).
Blain: "World's first graphene speaker already superior to Sennheiser MX400", htt://www.gizmag.com/graphene-speaker-beats-sennheiser-mx400/31660, (Apr. 15, 2014).
BMW, "BMW introduces BMW Connected—The personalized digital assistant", "http://bmwblog.com/2016/01/05/bmw-introduces-bmw-connected-the-personalized-digital-assistant", (Jan. 5, 2016).
BRAGI Is on Facebook (2014).
BRAGI Update—Arrival of Prototype Chassis Parts—More People—Awesomeness (May 13, 2014).
BRAGI Update—Chinese New Year, Design Verification, Charging Case, More People, Timeline(Mar. 6, 2015).
BRAGI Update—First Sleeves From Prototype Tool—Software Development Kit (Jun. 5, 2014).
BRAGI Update—Let's Get Ready to Rumble, A Lot to Be Done Over Christmas (Dec. 22, 2014).
BRAGI Update—Memories From April—Update on Progress (Sep. 16, 2014).
BRAGI Update—Memories from May—Update on Progress—Sweet (Oct. 13, 2014).
BRAGI Update—Memories From One Month Before Kickstarter—Update on Progress (Jul. 10, 2014).
BRAGI Update—Memories From The First Month of Kickstarter—Update on Progress (Aug. 1, 2014).
BRAGI Update—Memories From The Second Month of Kickstarter—Update on Progress (Aug. 22, 2014).
BRAGI Update—New People @BRAGI—Prototypes (Jun. 26, 2014).
BRAGI Update—Office Tour, Tour to China, Tour to CES (Dec. 11, 2014).
BRAGI Update—Status on Wireless, Bits and Pieces, Testing—Oh Yeah, Timeline(Apr. 24, 2015).
BRAGI Update—The App Preview, The Charger, The SDK, BRAGI Funding and Chinese New Year (Feb. 11, 2015).
BRAGI Update—What We Did Over Christmas, Las Vegas & CES (Jan. 19, 2014).
BRAGI Update—Years of Development, Moments of Utter Joy and Finishing What We Started(Jun. 5, 2015).
BRAGI Update—Alpha 5 and Back to China, Backer Day, On Track(May 16, 2015).
BRAGI Update—Beta2 Production and Factory Line(Aug. 20, 2015).
Bragi Update—Certifications, Production, Ramping Up.
BRAGI Update—Developer Units Shipping and Status(Oct. 5, 2015).
BRAGI Update—Developer Units Started Shipping and Status (Oct. 19, 2015).
BRAGI Update—Developer Units, Investment, Story and Status(Nov. 2, 2015).
BRAGI Update—Getting Close(Aug. 6, 2014).
BRAGI Update—On Track, Design Verification, How It Works and What's Next(Jul. 15, 2015).
BRAGI Update—On Track, On Track and Gems Overview.
BRAGI Update—Status on Wireless, Supply, Timeline and Open House@BRAGI(Apr. 1, 2015).
BRAGI Update—Unpacking Video, Reviews on Audio Perform and Boy Are We Getting Close(Sep. 10, 2015).
Healthcare Risk Management Review, "Nuance updates computer-assisted physician documentation solution" (Oct. 20, 2016).
Hoyt et. al., "Lessons Learned from Implementation of Voice Recognition for Documentation in the Military Electronic Health Record System", The American Health Information Management Association (2017).
Hyundai Motor America, "Hyundai Motor Company Introduces A Health + Mobility Concept for Wellness in Mobility", Fountain Valley, California (2017).
Last Push Before The Kickstarter Campaign Ends on Monday 4pm CET (Mar. 28, 2014).
Nigel Whitfield: "Fake tape detectors, 'from the stands' footie and UGH? Internet of Things in my set-top box"; http://www.theregister.co.uk/2014/09/24/ibc_round_up_object_audio_dlna_iot/ (Sep. 24, 2014).
Staab, Wayne J., et al., "A One-Size Disposable Hearing Aid is Introduced", The Hearing Journal 53(4):36-41) Apr. 2000.
Stretchgoal—It's Your Dash (Feb. 14, 2014).
Stretchgoal—The Carrying Case for The Dash (Feb. 12, 2014).
Stretchgoal—Windows Phone Support (Feb. 17, 2014).
The Dash + The Charging Case & The BRAGI News (Feb. 21, 2014).
The Dash—A Word From Our Software, Mechanical and Acoustics Team + An Update (Mar. 11, 2014).
Update From BRAGI—$3,000,000—Yipee (Mar. 22, 2014).

* cited by examiner

AUDIO ACCELEROMETRIC FEEDBACK THROUGH BILATERAL EAR WORN DEVICE SYSTEM AND METHOD

PRIORITY STATEMENT

This application claims priority to U.S. Provisional Patent Application 62/320,147, filed on Apr. 8, 2016, and entitled Audio Accelerometric Feedback through Bilateral Ear Worn Device System and Method, hereby incorporated by reference in its entirety.

FIELD OF THE INVENTION

The present invention relates to wearable devices. More particularly, but not exclusively, the present invention relates to earpieces.

BACKGROUND

Individuals who regularly engage in physical activities, such as athletes, require constant and significant feedback from many points of their bodies in order to properly function. Cephalic kinematics is one area that is important for proper body coordination and placement while performing physical activities, in fact, some believe that head movement may be the most important factor in coordinating proper body placement during physical activity. However, no system or device exists that optimizes head placement in order to maximize body coordination.

SUMMARY

In one implementation, a system includes at least one earpiece comprising at least one speaker disposed within the at least one earpiece, at least one sensor disposed within the at least one earpiece, and at least one processor operatively connected to the speakers and the sensors, wherein the at least one processor is configured to calculate a desired position of a user's head based on at least one movement reading of the user's head from the at least one sensor and to transmit a first audio signal derived from the at least one movement reading to the at least one speaker, wherein the first audio signal guides a user to the desired position of the user's head.

One or more of the following features may be included. The earpieces may consist of a set of earpieces configured to transmit the first audio signal to a user's tympanic membranes. The at least one processor may be configured to calculate a desired movement of the user's head based upon the at least one movement reading of the user's head from the at least one sensor and to transmit a second audio signal containing instructions derived from the at least one movement reading to the at least one speaker, wherein the second audio signal guides the user as to the desired movement of the user's head. In addition, the at least one processor may be configured to calculate the desired position of a user's head based on at least one external movement reading of another area of the user's body from at least one external sensor and to transmit a third audio signal containing instructions derived from the at least one movement reading and the at least one external movement reading to the at least one speaker, wherein the third audio signal guides the user as to the desired position of the user's head. Also, the first, second, and third audio signals may be calculated from a zero audio reference point.

In another implementation, a method includes determining, via at least one sensor disposed within at least one earpiece, a current orientation of a user's head based on at least one movement reading of a user's head from the at least one sensor. At least one processor operatively connected to the at least one earpiece calculates a desired position of the user's head based on the at least one movement reading of the user's head. The at least one processor creates a first audio signal containing instructions derived from the at least one movement reading of the user's head to guide a user to the desired position of the user's head. The at least one processor then transmits the first audio signal to at least one speaker disposed within the at least one earpiece. The at least one speaker then transmits the first audio signal to at least one of the user's ears.

One or more of the following may be included. The at least one earpiece may comprise a set of earpieces configured to transmit the first audio signal to a user's tympanic membranes. The at least one processor may further calculate a desired movement of the user's head based on the at least one movement reading of the user's head and create a second audio signal containing instructions derived from the at least one movement reading of the user's head to guide the user as to the desired movement of the user's head. The at least one processor may then transmit the second audio signal to the at least one speaker, which then transmits the second audio signal to the at least one of the user's ears. In addition, the at least one processor may calculate the desired position of a user's head based on at least one external movement reading of another area of the user's body from at least one external sensor, create a third audio signal containing instructions derived from the at least one movement reading and the at least one external movement reading and to transmit the third audio signal to the at least one speaker, wherein the third audio signal guides the user to the desired position of the user's head. Also, the first, second, and third audio signals may be calculated from a zero-audio reference point.

In another implementation, a system includes a left earpiece comprising at least one microphone and a speaker and a right earpiece comprising at least one microphone and a speaker, wherein the system is configured to assist in placement of a head of a user within a three-dimensional space. In another implementation, a method to assist a user in placement of a head of the user includes providing a set of earpieces comprising a left earpiece and a right earpiece, wherein the left earpiece and the right earpiece comprise at least one microphone and a speaker, determining an orientation of the head of the user using the set of earpieces, and providing audio feedback to the user through the set of earpieces to assist the user in placement of the head of the user.

According to another aspect an earpiece includes an earpiece housing, a speaker, an inertial sensor disposed within the earpiece housing, and at least one processor disposed within the earpiece housing and operatively connected to the speaker and the inertial sensor. The earpiece further includes a task profile stored on a non-transitory memory of the earpiece, wherein the task profile defines head orientation or movement associated with performing a task. The at least one processor is configured to compare measurements sensed with the inertial sensor with the task profile, and if the measurements sensed exceed preset thresholds, generate an audible signal at the speaker instructing a user of the earpiece to alter head position. The earpiece may further include a transceiver disposed within the earpiece housing and operatively connected to the at least one processor for communicating with at least one external sensor operatively connected to the user, wherein the transceiver receives kinematic information from the at least one external sensor. The task profile may be used to define orientation or movement associated with performing the task for at least one of a neck of the user, a set of shoulders of the user, a torso of a user, a set of hips of the user, and a set of feet of the user. The at least one processor may be further configured to compare measurements sensed with the at least one external sensor with the task profile and if the measurements sensed with the at least one external sensor exceed preset thresholds, and generate an audible signal at the speaker instructing the user of the earpiece to alter body position. The task may be associated with a sports task, a work task, or other task.

According to another aspect, a method for improving performance of a task using an earpiece is provided. The method includes sensing head orientation using an inertial sensor of the earpiece and evaluating by a processor of the earpiece the head orientation to determine if the head orientation exceeds one or more thresholds for performance of the task. If the head orientation or the movement exceeds one or more thresholds for performance of the task, then the method includes generating an audio signal to guide the user to alter the head orientation and transducing the audio signal at a speaker of the earpiece to guide the user to alter the head orientation as the user performs the task. The method may further include receiving a selection of the task from the user using a gestural user interface of the earpiece. The step of evaluating may include obtaining the one or more thresholds for performance of the task from a task profile stored on a non-transitory storage medium.

One or more of these and/or other objects, features, or advantages of the present invention will become apparent from the specification and claims that follow. No single embodiment need provide each and every object, feature, or advantage. Different embodiments may have different objects, features, or advantages. Therefore, the present invention is not to be limited to or by an objects, features, or advantages stated herein.

DETAILED DESCRIPTION

Figure 1:
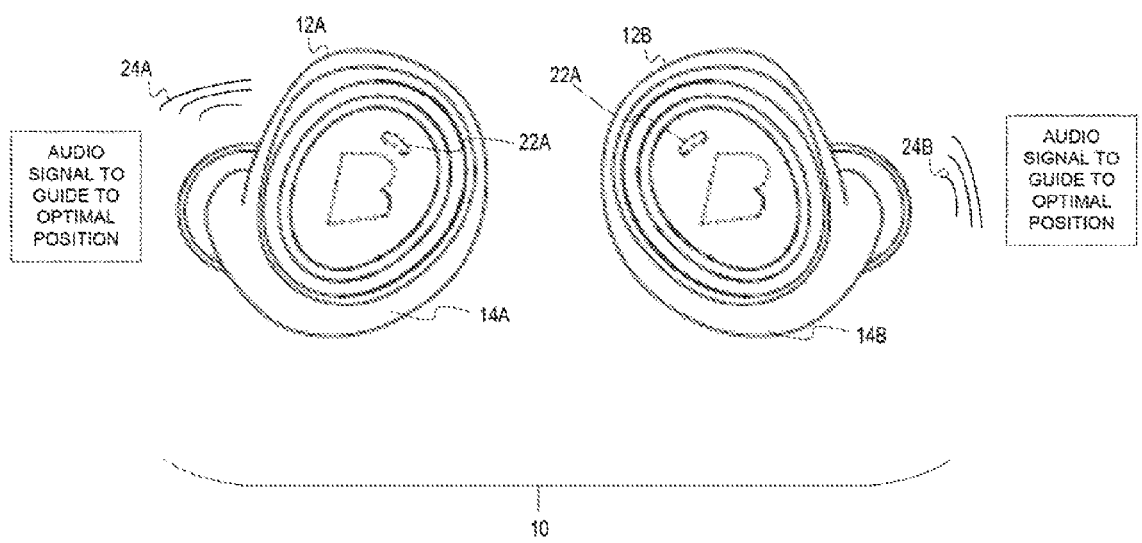
FIG. 1 illustrates a system which includes a left earpiece and a right earpiece.

FIG. 1 illustrates a system 10 which includes a left earpiece 12A and a right earpiece 12B. The left earpiece 12A has a left earpiece housing 14A. The right earpiece 12B has a right earpiece housing 14B. The left earpiece 12A and the right earpiece 12B as shown are configured to be placed within the external auditory canals of a user in an ear bud style configuration. However, other configurations of earpieces are contemplated including behind-the-ear configurations and head sets, and completely-in-the canal configurations. In die configuration shown, the earpieces 12A, 12B fit so as to physical block the external auditory canal, however other configurations may be used including those in which the canal remains fully open or partially open. An external microphone 22A is shown on the left earpiece 12A and an external microphone 22B is shown on the right earpiece 12B the external microphones 22A, 22B may be positioned so as to detect ambient sounds within the environment. The earpieces may include one or more sensors used to determine head position of the user and then to communicate audio signals 24A and 24B respectively to guide a user as to a desired placement of a user's head. The audio signals 24A and 24B may contain verbal instructions, sounds representing specific instructions that the user can follow, or sounds that stimulate certain areas of the user's ear canal or the user's tympanic membranes which can guide the user to the best placement of the user's head. One application for the system 10 is for use by athletes in sports that require precise coordination such as gymnastics and other similar Olympic sports, soccer, basketball, swimming, skiing, martial arts, and many others. Other applications may include tactical training, marksmanship, training operation of a vehicle or machine, and physical therapy. Of course, any number of other applications are contemplated where it is desirable to give a user feedback regarding placement of the user's head.

Figure 2:
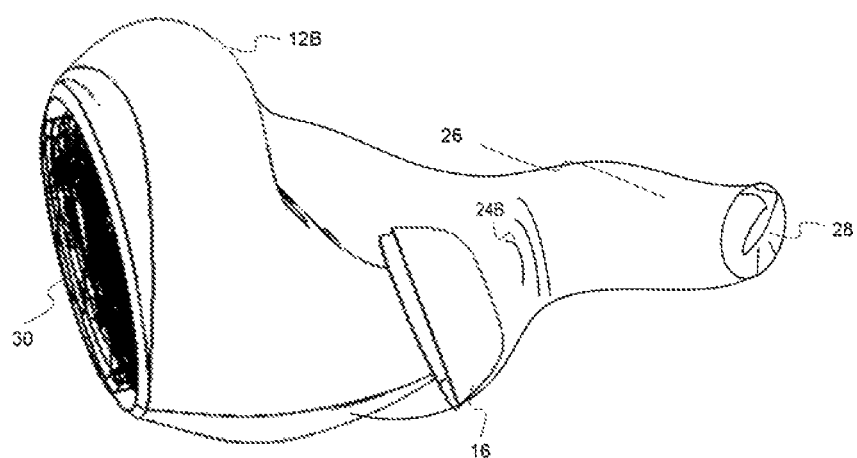
FIG. 2 illustrates a side view of a preferred embodiment of one of the earpieces and its relationship with a user's ear

FIG. 2 illustrates a side view of a right earpiece 12B and its relationship to a user's ear. The earpiece 12B is configured is fit comfortably within a user's ear canal 26 so as to both minimize the amount of external sound reaching the user's ear canal 26 and to facilitate the transmission of the audio signal 24B from the speaker 16 to a user's tympanic membrane 28. The earpiece 12B may be configured to be of any size necessary to fit within the user's ear canal 26 and sleeves may be used to assist with the fit or the earpiece may be custom molded. The earpiece 12B may also has a gesture control interface 30 in which the user can control the system 10. The gestures that may be used to control the system 10 include touching, tapping, swiping, use of an instrument, or any combination of the aforementioned gestures. Touching gestures used to control the system 10 may be of any duration and may include the touching of areas that are not part of the gesture control interface 30. Tapping gestures used to control the system 10 may include any number of taps and need not be brief. Swiping gestures used to control the system 10 may include a single swipe, a swipe that changes direction at least once, a swipe with a time delay, a plurality of swipes, or any combination of the aforementioned. The gestural control interface 30 may be performed in various ways such as using light emitters and detections, capacitive sensing, or other types of emitters and detectors. The gestural control interface 30 may be used by an individual to specify the type of activity or task that the user is performing or whether the user would like to receive feedback on head or body position or movement while performing one or more tasks or activities.

Figure 3:
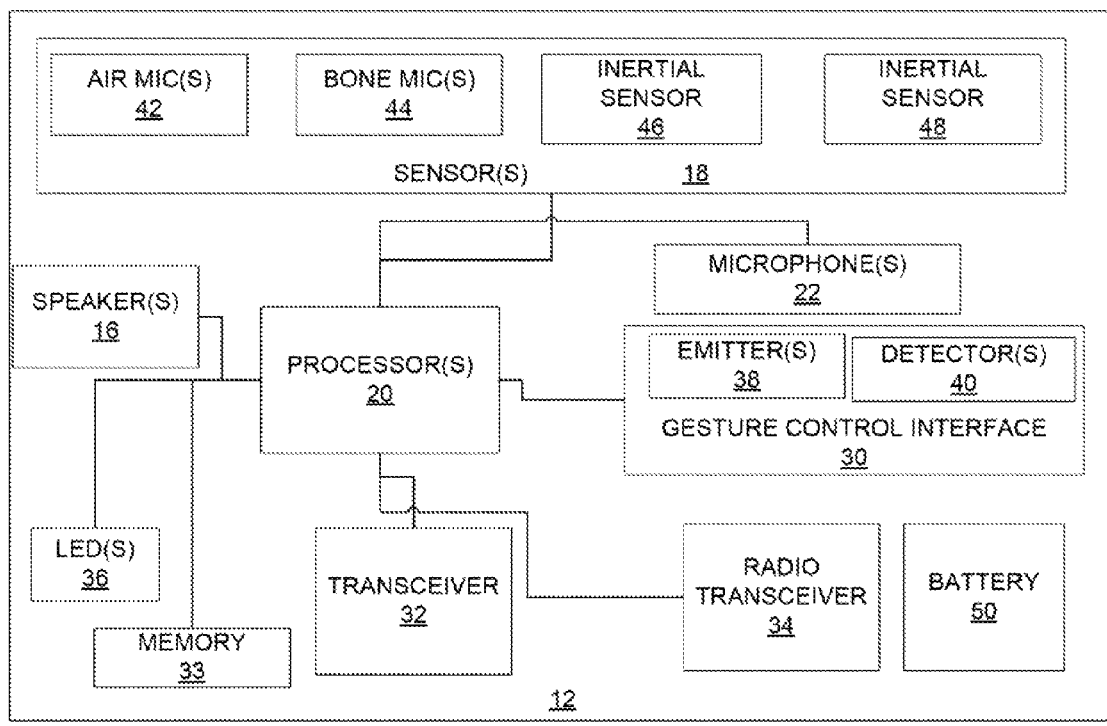
FIG. 3 illustrates a block diagram of the system.

FIG. 3 is a block diagram of the system 10 which comprises at least one earpiece 12, at least one speaker 16 disposed within the earpiece 12, at least one sensor 18 with at least one air microphone 42, at least one bone conduction microphone 44, and a plurality of inertial sensors 46, 48 operatively connected to the earpiece 12, at least one microphone 22 operatively connected to the earpiece 12, a gesture control interface 30 with at least one emitter 38 and at least one detector 40 operatively connected to the earpiece 12, a transceiver 32 disposed within the earpiece 12, a radio transceiver 34 disposed within the earpiece 12, at least one LED disposed within the earpiece 12, a battery 50 disposed within the earpiece 12 and operatively connected to all of the aforementioned components, and at least one processor 20 disposed within the earpiece 12 and operatively connected to all of the aforementioned components. The earpiece 12 may be composed of metal, plastic, composites, combinations thereof, or any other material suitable for human use and may be configured to both minimize the direct passage of ambient noise from the environment and to facilitate the reproduction of audio signals at a user's ear. The earpiece 12 may also be constructed to be waterproof.

One or more speakers 16 disposed within the earpiece 12 may be positioned proximate to a user's tympanic membrane and be configured to receive at least one audio signal from the one or more processors 20 and to transmit one or more audio signals while the earpiece is functional.

One or more sensors 18 operatively connected to the earpiece 12 may be configured to detect a user's cephalic movements and determine a current orientation of a user's head. The sensors 18 may also be configured to detect movements of other areas of a user's body, clothing or other objects worn by a user, a surface the user is standing on, or an external object not directly in contact with the user in addition to the user's head and may be located anywhere on the earpiece 12. The sensors 18 may also contain an air microphone 42 and/or a bone conduction microphone 44 for detecting sound from the interior of the user's head and/or ambient sound, or one or more inertial sensors 46, 48 for detecting inertial changes or to further improve the accuracy of the location of the user's head.

A memory 33 operatively connected to the one or more processors 20 is also shown. The memory 33 may be used to store task profiles associated with performing one or more tasks. For example, a task profile may include proper head orientation and/or head movement associated with performing a particular activity. The information stored as a part of a task profile may be used to compare a user's current head orientation or position while performing a particular task with what is acceptable, likely to lead to improved performance optimal, or otherwise desirable for performing the particular task.

One or more microphones 22 operatively connected to the earpiece 12 may be configured to receive audio inputs, where the audio inputs may originate from the user, a third-party, a machine, an animal, another earpiece, another electronic device, or even nature itself. The at least one microphone 22 need not be configured to receive every type of audio input. For example, one microphone may be configured to receive ambient environment audio inputs, and another microphone may be configured to receive audio inputs from the user such as speech.

The gesture control interface 30 operatively connected to the earpiece 12 is configured to allow the user to control the earpiece 12. The gesture control interface 30 may include at least one emitter 38 and at least one detector 40 to detect gestures from either the user, a third-party, an instrument, or a combination of the aforementioned and transmit one or more gestures to one or more processors 20. The gestures that may be used with the gesture control interface 30 to control the earpiece 12 include, without limitation, touching, tapping, swiping, use of an instrument, or any combination of the aforementioned gestures. Touching gestures used to control the earpiece 12 may be of any duration and may include the touching of areas that are not part of the gesture control interface 30. Tapping gestures used to control the earpiece 12 may include any number of taps and need not be brief. Swiping gestures used to control the earpiece 12 may include a single swipe, a swipe that changes direction at least once, a swipe with a time delay, a plurality of swipes, or any combination of the aforementioned. The user interface may be used to identify a particular task which the user is performing or will perform, indicate when the task is complete, or indicate that the user seeks feedback on their head or body position when performing the particular task. Of course, other types of user interfaces may be used including voice control interfaces.

The transceiver 32 disposed within the earpiece 12 may be configured to receive signals from and to transmit signals to a second earpiece of the user if the user is using more than one earpiece. The transceiver 32 may receive or transmit more than one signal simultaneously. The transceiver 32 may be of any number of types including a near field magnetic induction (NFMI) transceiver. The radio transceiver 34 disposed within the earpiece 12 is configured to receive signals from external electronic devices and to transmit those signals to the at least one processor 20. The external electronic devices the radio transceiver 34 is configured to receive signals from may include Bluetooth devices, mobile devices, desktops, laptops, tablets, modems, routers, communications towers, cameras, watches, third-party earpieces, wearable devices, and other electronic devices capable of transmitting wireless signals. The radio transceiver 34 may receive or transmit more than one signal simultaneously.

The earpiece may communicate with one or more other body worn sensors including through the transceiver 32 or the radio transceiver 34. Where other body worn sensors are used, the body worn sensors may provide additional kinematic data regarding body position. For example, a body worn sensor may be in the form of a watch or wristband and may include an inertial sensor. Similarly body worn sensors may be integrated into clothing, footwear, jewelry, fashion accessories, or otherwise, to sense orientation or movement of the body including a neck of the user, a set of shoulders of the user, a torso of a user, a set of hips of the user, and a set of feet of the user. The measurements may then be communicated to the earpiece and used to determine a user's deviations from a task profile.

The LEDs 36 disposed within the earpiece 12 may be configured to emit light in order to convey to the user information concerning the earpiece 12. The LEDs 36 may be located in any area on the earpiece 12 suitable for viewing by the user or a third-party and may consist of as few as one diode. In addition, the LEDs 36 may be discernable by a human eye or an electronic device and need not have a minimum luminescence.

The battery 50 of the earpiece 12 is operatively connected to all of the components within the earpiece 12. The battery 50 may provide enough power to operate the earpiece 12 for a reasonable duration of time. The battery 50 may be of any type suitable for powering the earpiece 12. However, the battery 50 need not be present in the earpiece 12. Alternative power sources may be used to power the earpiece 12.

One or more processors 20 are operatively connected to each component within the earpiece 12 and configured to receive measurements from one or more sensors 18 and use those measurements to determine a desired position of the user's head and variation with a task profile. The processors 20 may also be configured to receive signals from components other than the sensors 18, such as one or more microphones 22, the transceiver 32, the radio transceiver 34, or an external sensor not physically connected to the earpiece 12 in order to calculate the desired location for the user's head. It is also possible that the user's head may not need to be moved after calculation by the one or more processors 20. The processor(s) 20 are also configured to create a first audio signal containing instructions derived from the information conveyed by the sensors 18 to guide the user to the desired position of the user's head and to communicate the first audio signal to the speakers 16. The first audio signal may also incorporate information from one or more microphones 22, the transceiver 32, or the radio transceiver 34 to improve the accuracy of the desired location for the user's head. In addition, one or more processors 20 may be configured to calculate a desired movement of the user's head from signals conveyed by one or more sensors 18 in order to create a second audio signal containing instructions derived from the information conveyed by the sensors 18 to guide the user as to the desired position of the user's head and to transmit the second audio signal to the speakers 16. Like the first audio signal, the second audio signal may also incorporate information from one or more microphones 22, the transceiver 32, or the radio transceiver 34 to improve the accuracy of the desired movement of the user's head. In addition, one or more processors 20 may be configured to calculate the desired position of the user's head using signals concerning other parts of the user's body, clothing or other objects worn by the user, a surface the user is standing on, an external object not directly in contact with the user, or a combination of the aforementioned in addition to signals concerning the user's head conveyed by one or more sensors 18 or by one or more external sensors in order to create a third audio signal containing instructions derived from the information conveyed by the sensors 18 or one or more external sensors to guide the user to the desired location of the user's head and to transmit the third audio signal to the speakers 16. The signals conveyed to the at least one processor 20 by the one or more sensors 18 or the one or more external sensors need not be in any order. Like the previous two signals, the third audio signal may also incorporate information from one or more microphones 22, the transceiver 32, or the radio transceiver 34 to improve the accuracy of the desired location for the user's head.

The guidance provided by the earpiece may be for the user to tilt their head up, to turn their head to the left or to the right, to tilt their head down, to lift their head up, to lower their head, to tilt their head to one side or the other, or combinations of these or other head movements which will guide the head from a current position to a desired position. Therefore, the processor may convert specific measurements such as degrees into more understandable language such as "Turn your head slightly towards the left", "Eyes forward", "Look up", "Slowly move your head down and towards the right." "Move your head to the left until I say stop. Stop." It is to also be understood that the audio guidance need not be verbal. For example, a sound can be played which changes pitch or volume until the user moves their head to the proper position.

Figure 4:
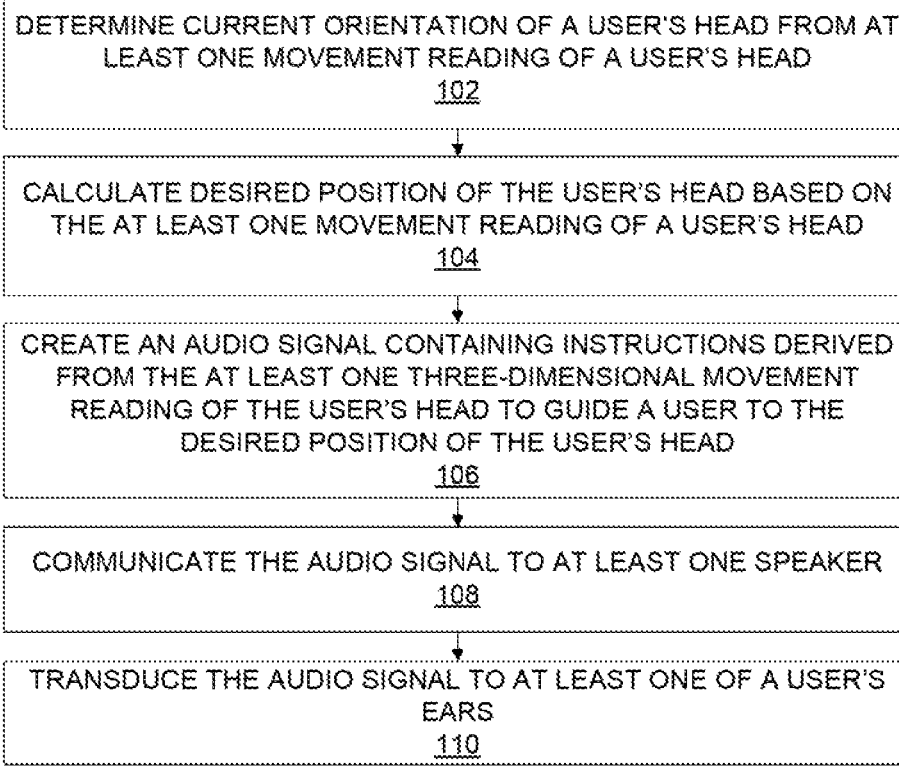
FIG. 4 includes a flowchart of one implementation of the method.

FIG. 4 illustrates a flowchart of one example of a method 100 of the invention. At least one sensor determines 102 a current orientation of a user's head from at least one movement reading of the user's head by the at least one sensor. The user's head may be stationary or in motion, and the at least one movement reading of the user's head may be either two-dimensional or three-dimensional, and may include one or more data points. At least one processor then calculates 104 a desired position of the user's head based on the at least one movement reading of the user's head. The user's head does not necessarily have to be moved from its current position and the calculation 104 may incorporate data in addition to the at least one movement reading to ascertain the desired position of the user's head. The at least one processor then creates 106 a first audio signal which contains instructions derived from the at least one movement reading of the user's head to guide the user to the desired position of the user's head. The first audio signal may be of any intensity that does not cause undue harm to the user's tympanic membranes and the instructions may be verbal instructions, sounds associated with specific instructions known or knowable by the user, sounds which coax the head of the user to its desired position without conscious input by the user, or a combination of the aforementioned. The at least one processor then communicates 108 the first audio signal to at least one speaker. The first audio signal may be disaggregated into multiple signals and communicated 108 to more than one speaker if multiple instructions are involved. The at least one speaker then transduces 110 the first audio signal at least one of a user's ears. The first audio signal may be continuous or discontinuous.

It is also contemplated that a record of the user's head positions, head movement, and guidance or corrections provided may be stored in either the earpieces or at a connected device such as a mobile device. This may be further processed to provide additional insight regarding a user's performance in a particular task. It may also be used to predict a user's head movement in response to a particular stimuli so that the guidance process may begin earlier or even pre-emptively.

Where both a left earpiece and a right earpiece are present, position, orientation and movement of a human head may be tracked in a variety of ways including through monitoring pitch, roll, and yaw. Pitch may be considered movement of the head forward or back. Roll my be considered movement tilting the head from side to-side, and yaw may be considered turning left and right. The inertial sensor may include a 3-axis accelerometer, a 3-axis gyroscope, an a 3-axis magnetometer. Having an inertial sensor in both the right and left earpiece allows for greater accuracy then in one ear piece.

Various tasks may have preferred position or movement profiles associated with them as a task profile. These profiles may be determined in various ways including from simply observing sensed data from one or more experts performing the tasks in what they believe to be the correct manner. A profile may also be created from a user performing a task in a particularly successful manner, or may be constructed individually for a user. In operation, a comparison is made between the position or movement of the user's head and one or more positions or movements associated with the task profile. If the difference in position exceeds a preset criteria or threshold, then the user is guided by the earpieces to adjust their head position to the desired head position. Similarly, if the earpiece is in communication with other body worn sensors than the profile may contain position or movement for other parts of the body. In operation, a comparison is made between the position or movement of the user's body and one or more positions or movements associated with the task profile. If the difference in position exceeds a preset criteria or threshold, then the user is guided by the earpieces to adjust their body position to the desired body position such as through audio feedback from the earpiece.

Therefore, various methods, systems, and apparatus have been shown and described for allowing for one or more earpieces to provide feedback to a user regarding their bead and/or body placement. Although various specific examples have been shown and described, it is to be understood that the present invention contemplates variations in the structure and components of the earpieces and the methods in which user head or body position is determined and in the manner in which feedback is provided.

What is claimed is:

1. An ear piece, comprising:
   an earpiece housing;
   a speaker;
   an inertial sensor disposed within the earpiece housing, the inertial sensor comprising a 3-axis accelerometer and a 3-axis gyroscope;
   at least one processor disposed within the earpiece housing and operatively connected to the speaker and the inertial sensor;
   a task profile stored on a non-transitory memory of the earpiece, wherein the task profile defines head orientation and movement associated with performing a task;
   wherein the at least one processor is configured to compare measurements sensed with the inertial sensor with the task profile, and if the measurements sensed exceed preset thresholds, calculate a desired position of the head orientation and generate an audible signal at the speaker instructing a user of the earpiece to alter head position to the desired head orientation position.

2. The earpiece of claim 1 further comprising a transceiver disposed within the earpiece housing and operatively connected to the at least one processor for communicating with at least one external sensor operatively connected to the user, wherein the transceiver receives kinematic information from the at least one external sensor.

3. The earpiece of claim 2 wherein the task profile further defines orientation or movement associated with performing the task for at least one of a neck of the user, a set of shoulders of the user, a torso of a user, a set of hips of the user, and a set of feet of the user.

4. The earpiece of claim 3 wherein the at least one processor is further configured to compare measurements sensed with the at least one external sensor with the task profile and if the measurements sensed with the at least one external sensor exceed preset thresholds, generate an audible signal at the speaker instructing the user of the earpiece to alter body position.

5. The earpiece of claim 1 wherein the task is associated with performing a sport.

6. A system comprising a left ear piece and a right earpiece and wherein one of the left earpiece and the right earpiece is the earpiece of claim 1.

7. A method for improving performance of a task using an earpiece, the method comprising steps of:
   sensing head orientation using an inertial sensor of the earpiece, the inertial sensor comprising a 3-axis accelerometer and a 3-axis gyroscope;
   evaluating by a processor of the earpiece the head orientation to determine if the head orientation exceeds one or more thresholds for performance of the task;
   if the head orientation or the movement exceeds one or more thresholds for performance of the task, then generating an audio signal instruction which guides the user to alter the head orientation to a specific position based upon the task being performed; and
   transducing the audio signal instruction at a speaker of the earpiece to guide the user to alter the head orientation as the user performs the task.

8. The method of claim 7 further comprising receiving a selection of the task from the user using a gestural user interface of the earpiece.

9. The method of claim 7 wherein the step of evaluating comprises obtaining the one or more thresholds for performance of the task from a task profile stored on a non-transitory storage medium.

10. An ear piece, comprising:
    an earpiece housing;
    a speaker;
    an inertial sensor disposed within the earpiece housing, the inertial sensor comprising a 3-axis accelerometer and a 3-axis gyroscope;
    at least one processor disposed within the earpiece housing and operatively connected to the speaker and the inertial sensor; and
    a task profile stored on a non-transitory memory of the earpiece, wherein the task profile defines head orientation and movement associated with performing a task requiring proper head orientation and head movement associated with performing any of at least one particular activity;
    wherein the at least one processor is configured to compare measurements sensed with the inertial sensor with the task profile, and if the measurements sensed exceed preset thresholds, generate an audible signal at the speaker instructing a user of the earpiece to alter head position.

11. The earpiece of claim 10 further comprising a transceiver disposed within the earpiece housing and operatively connected to the at least one processor for communicating with at least one external sensor operatively connected to the user, wherein the transceiver receives kinematic information from the at least one external sensor.

12. The earpiece of claim 11 wherein the task profile further defines at least one of orientation and movement associated with performing the task for at least one of a neck of the user, a set of shoulders of the user, a torso of a user, a set of hips of the user, and a set of feet of the user.

13. The earpiece of claim 12 wherein the at least one processor is further configured to compare measurements sensed with the at least one external sensor with the task profile and if the measurements sensed with the at least one external sensor exceed preset thresholds, generate an audible signal at the speaker instructing the user of the earpiece to alter body position.

14. The earpiece of claim 10 wherein the task is associated with performing a sport.

15. The earpiece of claim 14 wherein the sport is skiing.

16. A system comprising a left ear piece and a right earpiece and wherein one of the left earpiece and the right earpiece is the earpiece of claim 10.

* * * * *

UNITED STATES PATENT AND TRADEMARK OFFICE
CERTIFICATE OF CORRECTION

PATENT NO. : 10,015,579 B2
APPLICATION NO. : 15/481623
DATED : July 3, 2018
INVENTOR(S) : Peter Vincent Boesen Page 1 of 1

It is certified that error appears in the above-identified patent and that said Letters Patent is hereby corrected as shown below:

On the Title Page

Abstract, Line 5, change "it" to --includes--

Signed and Sealed this
Twenty-eighth Day of May, 2019

Andrei Iancu
*Director of the United States Patent and Trademark Office*